US011781991B2

United States Patent
Nakajima et al.

(10) Patent No.: US 11,781,991 B2
(45) Date of Patent: Oct. 10, 2023

(54) METHOD FOR DETECTING PROTEIN

(71) Applicant: MEIJI CO., LTD., Tokyo (JP)

(72) Inventors: Akihiro Nakajima, Tokyo (JP); Keiko Morikubo, Tokyo (JP)

(73) Assignee: MEIJI CO., LTD., Tokyo (JP)

( * ) Notice: Subject to any disclaimer, the term of this patent is extended or adjusted under 35 U.S.C. 154(b) by 497 days.

(21) Appl. No.: 16/762,653

(22) PCT Filed: Nov. 9, 2018

(86) PCT No.: PCT/JP2018/041722
§ 371 (c)(1),
(2) Date: May 8, 2020

(87) PCT Pub. No.: WO2019/093495
PCT Pub. Date: May 16, 2019

(65) Prior Publication Data
US 2020/0371036 A1    Nov. 26, 2020

(30) Foreign Application Priority Data
Nov. 10, 2017 (JP) ................... 2017-216909

(51) Int. Cl.
*G01N 21/78* (2006.01)
*G01N 21/25* (2006.01)
(Continued)

(52) U.S. Cl.
CPC ........... *G01N 21/78* (2013.01); *G01N 21/251* (2013.01); *G01N 33/04* (2013.01); *G01N 33/08* (2013.01); *G01N 33/12* (2013.01)

(58) Field of Classification Search
CPC ...... G01N 21/78; G01N 21/251; G01N 33/04; G01N 33/08; G01N 33/12; G01N 33/52; G01N 33/68
See application file for complete search history.

(56) References Cited

U.S. PATENT DOCUMENTS

| 5,714,127 A * | 2/1998 | DeWitt ................ C07K 1/045 422/534 |
| 2005/0147720 A1 | 7/2005 | Yamada et al. |

(Continued)

FOREIGN PATENT DOCUMENTS

| JP | 2-36355 | 2/1990 |
| JP | 5-312809 | 11/1993 |

(Continued)

OTHER PUBLICATIONS

International Search Report, dated Jan. 29, 2019 in corresponding International Patent Application No. PCT/JP2018/041722.
(Continued)

*Primary Examiner* — Dennis White
(74) *Attorney, Agent, or Firm* — Wenderoth, Lind & Ponack, LLP

(57) ABSTRACT

An object of the present invention is to provide a simple method of detecting a protein in a liquid, which requires less labor or cost as compared with a conventional method. In the present invention, it has been found that coloring a protein by a color reaction specific to the protein, performing filtration using a filter which easily adsorbs a protein to concentrate the protein on the filter, and checking coloration allows for simply and easily detecting and measuring a protein. In addition, it has been found that filtering a protein using a filter, concentrating the protein on the filter, then coloring the protein by a color reaction specific to the protein, and checking the protein allows simply and easily detecting and measuring a protein.

9 Claims, 12 Drawing Sheets

(51) Int. Cl.
*G01N 33/04* (2006.01)
*G01N 33/08* (2006.01)
*G01N 33/12* (2006.01)

(56) References Cited

U.S. PATENT DOCUMENTS

| | | | |
|---|---|---|---|
| 2005/0191704 A1* | 9/2005 | Boga | G01N 33/523 435/7.1 |
| 2017/0184506 A1* | 6/2017 | Patel | G01N 21/78 |

FOREIGN PATENT DOCUMENTS

| | | | | |
|---|---|---|---|---|
| JP | 11-304803 | | 11/1999 | |
| JP | 2006-349650 | | 12/2006 | |
| JP | 2006349650 | A * | 12/2006 | |
| JP | 2010-223726 | | 10/2010 | |
| JP | 2010223726 | A * | 10/2010 | |
| JP | 2017-129422 | | 7/2017 | |
| JP | 2017129422 | A * | 7/2017 | G01N 33/50 |
| WO | 2004/011948 | | 2/2004 | |

OTHER PUBLICATIONS

Kinoshita et al., "Fluorescence analysis of proteins on a membrane filter, using fluorescein isothiocyanate dissolved in the cycloheptaamylose guanidine system", Bunseki Kagaku, 23(12): 1543-1544 (1974)—English Abstract.

Notice of Reasons for Refusal dated Jun. 14, 2022 in corresponding Japanese Patent Application No. 2019-552411, with English-language translation.

Notice of Reasons for Refusal dated Nov. 8, 2022 in Japanese Application No. 2019-552411, with English translation thereof.

Decision of Refusal issued May 30, 2023 in corresponding Japanese Patent Application No. 2019-552411, with English language translation.

Bradford Method (Residual Protein) https://www.jfrl.or.jp/storage/file/748.pdf.

* cited by examiner (A)

(B)

METHOD FOR DETECTING PROTEIN

TECHNICAL FIELD

The present invention relates to a method for detecting a protein, a method for calculating a protein concentration, and a protein detection kit. In particular, the present invention relates to a method for detecting a protein in a liquid, a method for calculating a protein concentration in a liquid, and a kit for detecting a protein in a liquid.

BACKGROUND ART

In a food industry, for the purpose of preventing an allergen (allergic substance) contained in one food product from getting mixed in with another food product, it is necessary to grasp an amount of the allergen in rinse water after cleaning of a production facility or the like. In general, since an allergen is a protein in many cases, an enzyme immunoassay method (ELISA method) is used for detection and measurement of the allergen. However, the ELISA method is a method of detecting a specific allergen using an antibody, and a detectable and/or measurable protein is limited. It lacks versatility.

Thus, methods capable of simply detecting more allergens have been widely examined. For example, International Publication No. WO2004/011948 (Patent Document 1) describes a method of analyzing a protein, including a combination of a dot-blotting method and a fluorescent staining method.

RELATED ART

Patent Document

[Patent Document 1] International Publication No. WO2004/011948

DISCLOSURE OF INVENTION

Problems to be Solved by the Invention

As described above, the ELISA method or the like has been known so far as a method for detecting an allergen (protein). However, it takes labor and cost because an operation is complicated and a kit or the like is also required. Therefore, the ELISA method is difficult to be adopted as a method of checking a degree of cleanliness of rinse water for a production facility or the like, which is performed every day in a food production factory, for example.

On the other hand, a turbidimetric method has been known as a simple method of detecting an allergen (protein). However, in this method, turbidity due to components (oils and fats or the like) other than a protein is also detected as a protein, and thus excessive cleaning of the production facility or the like is required.

In addition, the technique disclosed in Patent Document 1 has problems that it requires a special fluorescent image analyzer to perform the fluorescent staining method, and that it requires 4 to 5 hours from sample preparation to image analysis and thus rapid detection of an allergen (protein) at a site of food production is difficult.

Accordingly, an object of the present invention is to provide a simple and easy method for detecting a protein which requires less labor and cost as compared with a conventional method. Furthermore, another object of the present invention is to provide a method for calculating a concentration of the detected protein, and a protein detection kit capable of simply detecting a protein.

Means for Solving the Problems

In order to achieve the above-mentioned objects, the present inventors reviewed and examined a method of pretreatment of a measurement sample and the like so as to construct a simple and easy method for detecting a protein. As a result, surprisingly, they have found that even a low-concentration protein can be simply and easily detected and measured by coloring a target protein to be measured by a color reaction specific to the protein, then performing filtration using a filter to retain and concentrate the protein on the filter, and checking coloration visually or with a differential colorimeter or the like.

In addition, they also have found that the target protein to be measured can be simply and easily detected and measured by filtering the target protein to be measured using a filter to be concentrated on the filter, then coloring the protein by a color reaction specific to the protein, and checking the protein visually or with a differential colorimeter or the like.

In addition, the present inventors have found a constant correlation between a concentration of the target protein to be measured in a sample and a color value of coloration of the detected target protein to be measured. Accordingly, they have found that a concentration of the target protein to be measured can be calculated from a color value obtained by the measurement by creating in advance a calibration curve indicating a correspondence between the concentration of the target protein to be measured and the color value thereof.

Furthermore, the present inventors have found a protein detection kit capable of performing the above-described simple and easy method for detecting a protein.

That is, the present invention is as follows.

[1]

A method for detecting a protein comprising a coloration step of coloring a target protein to be measured, a filtration step of filtering the target protein to be measured with a filter and a detection step of detecting coloration of the target protein to be measured on the filter.

[2]

The detection method according to [1], wherein the coloration step, the filtration step, and the detection step are performed in this order.

[3]

The detection method according to [1], wherein the filtration step, the coloration step, and the detection step are performed in this order.

[4]

The detection method according to any one of [1] to [3], wherein in the coloration step, coloration of the target protein to be measured is performed by using a reagent for measurement causing a shift of an absorbance wavelength by binding to the target protein to be measured.

[5]

The detection method according to [4], wherein the coloration step is a coloration step of coloring the target protein to be measured by a Bradford method.

[6]

The detection method according to any one of [1] to [5], wherein the filtration step is a filtration step of filtering the target protein to be measured with a glass filter.

[7]

The detection method according to any one of [1] to [6], wherein the target protein to be measured is a protein in rinse water at the time of cleaning in a food production factory.

[8]

The detection method according to [7], wherein the protein in the rinse water at the time of cleaning in the food production factory is gelatin or collagen.

[9]

The detection method according to any one of [1] to [8], wherein a time required for detection is 1 hour or shorter.

[10]

A method for calculating a protein concentration comprising, a coloration step of coloring a target protein to be measured, a filtration step of filtering the target protein to be measured with a filter, a detection step of detecting coloration of the target protein to be measured on the filter and a measurement step of measuring a color value of the coloration of the target protein to be measured which is detected in the detection step, wherein a concentration of the target protein to be measured is calculated from the color value measured in the measurement step by using a plurality of reference samples in which a concentration of a target protein to be measured and a color value thereof are known and creating a calibration curve indicating a correspondence between the concentration of the target protein to be measured and the color value in each reference sample.

[11]

A method for calculating a protein concentration comprising, a coloration step of coloring a target protein to be measured by a Bradford method, a filtration step of filtering the target protein to be measured with a filter, a detection step of detecting coloration of the target protein to be measured on the filter and a measurement step of measuring a b value defined in a L*a*b* color system based on a CIE standard for the coloration of the target protein to be measured which is detected in the detection step, wherein a concentration of the target protein to be measured is calculated from the b value measured in the measurement step by using a plurality of reference samples in which a concentration of a target protein to be measured and a b value defined in the L*a*b* color system based on the CIE standard are known and creating a calibration curve indicating a correspondence between the concentration of the target protein to be measured and the b value in each reference sample.

[12]

A protein detection kit comprising, a coloring unit which colors a target protein to be measured, a filtering unit which filters the target protein to be measured with a filter and a detecting unit which detects coloration of the target protein to be measured on the filter, wherein the protein detection kit is configured to enable detection of the protein from a coloration state of the filter.

[13]

The protein detection kit according to [12], further comprising, a coloration determination sheet, wherein the protein detection kit is for measuring a concentration of the target protein to be measured by comparing the coloration determination sheet with a coloration state in the detecting unit.

Effects of the Invention

The method for detecting a protein and the detection kit of the present invention allow for simply and easily detecting and measuring a protein. In particular, they allow for simply and easily detecting and measuring allergens, such as gelatin and collagen, for which a simple measurement method is not known and various other allergens, with reduced labor or cost.

In addition, the method for calculating a protein concentration of the present invention allows for easily calculating concentrations of various proteins in a sample.

Furthermore, the detection using the detection method of the present invention or the detection kit of the present invention requires about 1 hour at most, and thus the protein can be rapidly detected as compared with the ELISA method, the fluorescent staining method, or the like. This can greatly contribute to, for example, quality determination of cleanability of a production line (production facility) in a food factory.

EMBODIMENTS FOR CARRYING OUT THE INVENTION

Figure 1:
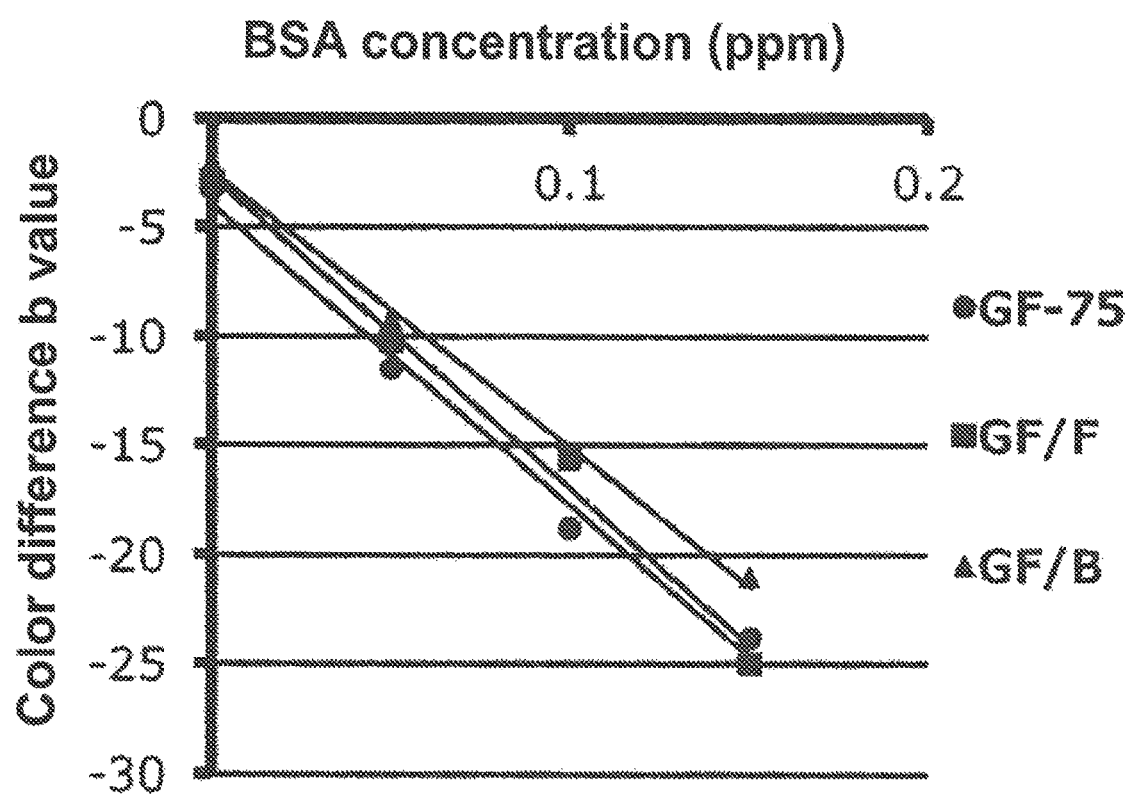
FIG. 1 is a graph showing results obtained by measuring a bovine serum albumin solution by the detection method of the present invention using three types of filters and measuring blue coloration as a b value with a differential colorimeter in Example 1.

The detection method of the present invention includes a coloration step, a filtration step, and a detection step.

First, the coloration step will be described. The coloration step is a step of coloring a target protein to be measured. A method of coloring a protein is not limited as long as coloration can be detected in a separately performed detection step. In particular, a method of coloring a target protein to be measured by using a measurement reagent of which an absorption wavelength is shifted due to binding to the target protein to be measured is advantageous for enhancing the effects of the present invention.

Example of the method of coloring a protein includes a Bradford method. This method is a method of quantifying a colored protein by utilizing the fact that binding of Coomassie Brilliant Blue which is an acid dye to the target protein to be measured leads to the shift of an absorption wavelength of the dye from 465 nm to 595 nm (from brown to blue). The coloration by the Bradford method is easily checked with naked eyes and is simply and easily detected. Thus, in the coloration step of the present invention, it is preferable to use the Bradford method. For the Bradford method, for example, Takara Bradford Protein Assay Kit (manufactured by Takara Bio Inc.) can be used.

Next, the filtration step will be described. The filtration step is a step of filtering the target protein to be measured with a filter and retaining and concentrating the target protein to be measured on the filter. The filter for filtering is not limited as long as the filter can retain the target protein to be measured. Examples thereof include a filter (glass filter or the like) on which the target protein to be measured can be physically collected to be concentrated; a filter to which the target protein to be measured can be chemically adsorbed; and a filter to which the target protein to be measured can be electrically adsorbed. In the filtration step in the present invention, it is preferable to use a glass filter, for example.

Specifically, a retained particle diameter of the glass filter is preferably 0.3 μm to 1.6 μm and more preferably 0.3 μm to 1.0 μm. The retained particle diameter means a diameter of a particle capable of being retained at 90% or more when class 7 powder-dispersed water specified in JIS Z 8901 is naturally filtered.

A filtration diameter of the glass filter is preferably 3 mm or more, more preferably 5 mm or more, and still more preferably 7 mm or more. Moreover, 40 mm or less is preferable, 35 mm or less is more preferable, and 33 mm or less is still more preferable. The filtration diameter of the glass filter means a diameter of a portion of the glass filter where a sample is actually filtered.

Furthermore, when the conditions for the glass filter are satisfied, an amount of a passed liquid is preferably 10 ml to 100 ml. Moreover, a time for passing the liquid can be appropriately adjusted according to a concentration of the sample or a flow rate at which a liquid is passed, and is usually 5 seconds to 40 minutes.

In addition, a filtration method is not particularly limited, and examples thereof include natural filtration, vacuum filtration, pressure filtration, and centrifugal filtration. From a viewpoint that a low-concentration protein can be simply and easily detected and measured, it is preferable to perform vacuum filtration by suction filtration.

Subsequently, the detection step will be described. The detection step is a step of detecting the target protein to be measured on the filter after coloration. In the detection step, retaining and concentrating the target protein to be measured which is colored on the filter through the coloration step and the filtration step allows for detecting the target protein to be measured. The detection method is usually performed in an optimal manner according to the coloration method. For example, the detection can be performed on the filter on which the protein is retained and concentrated by using a spectrophotometer or a differential colorimeter. Moreover, the detection may be performed using a coloration determination sheet as described later.

For one embodiment of the detection method of the present invention, the coloration step, the filtration step, and the detection step are performed in this order. In this case, specifically, the target protein to be measured is colored by a color reaction specific to the protein and filtered using a filter, and coloration of the target protein to be measured concentrated on the filter is detected (checked) visually or with a differential colorimeter or the like. By performing in the above-described order, the embodiment has an advantage that a small amount of the protein can be visually determined or numerically expressed.

In another embodiment of the detection method of the present invention, the filtration step, the coloration step, and the detection step are performed in this order. In this case, specifically, the target protein to be measured is filtered using a filter, the protein to be measured concentrated on the filter is colored by a color reaction specific to the protein, and the coloration is detected (checked) visually or with a differential colorimeter or the like. By performing in the above-described order, the embodiment has an advantage that extra dyes not bound to the protein can be removed from the filter.

The detection method of the present invention is very useful, in particular, as a method of checking a degree of cleanliness of rinse water, which is performed every day in a food production factory. A protein of an allergen in the rinse water can be very simply and rapidly detected with less labor and cost as compared with conventional methods such as the ELISA method, the turbidimetric method, and the fluorescent staining method. Specifically, according to the detection method of the present invention, a time required for detection can be 1 hour or shorter. Furthermore, the time required for detection means a time from when a test instrument is installed until a detection result is obtained. Moreover, according to a kit described later, the time required for detection can be further reduced.

A kind of the allergen (protein) to be measured which can be detected by the detection method of the present invention is not limited, and examples thereof include allergens contained in an egg, milk, wheat, buckwheat, a peanut, and a crustacean, in addition to gelatin and collagen. Specific examples thereof include ovalbumin, casein, gliadin, a partially purified buckwheat protein, a partially purified peanut protein, and crustacean tropomyosin.

The detection method of the present invention is very useful, in particular, for detecting gelatin or collagen as the target allergen (protein) to be measured. For example, the detection limit of gelatin or collagen by measuring equipment (for example, HPLC) is said to be 40 ppb. However, in the detection method of the present invention, gelatin having a concentration of 1 to 30 ppb can also be detected. Therefore, the present invention is very useful for detecting gelatin or collagen, which is a protein of an allergen that has been difficult to detect so far.

Moreover, other proteins (milk allergen, egg allergen, or the like) can also be detected in a wide range of concentrations, including a low concentration.

The sample used in the detection method of the present invention is not limited, but is preferably a liquid. For the liquid, for example, factory water, particularly, rinse water used for cleaning of a production facility in a food factory is preferably used from a viewpoint of the effects of the present invention.

Adding an appropriate neutralizer to a measurement target in advance allows the detection method of the present invention to be applied to, for example, a solution having chlorine in high concentration, such as factory water. As the neutralizer, for example, sodium ascorbate, sodium thiosulfate, and the like can be suitably used.

Furthermore, the present invention provides a method of calculating a concentration of the target allergen (protein) to be measured in the sample through a measurement step of measuring a color value for a coloration state of the target protein to be measured which is detected in the detection step, in addition to the coloration step, the filtration step, and the detection step in the detection method.

The examination of the present inventors, as shown in examples described later, has revealed a constant correlation between the concentration of the target allergen (protein) to be measured in the sample and the color value of the coloration of the target protein to be measured which is detected in the above-described detection step. In particular, a linear relation (linear function) between the concentration of the target allergen (protein) to be measured and the color value of the coloration of the target protein to be measured has been turned out.

Therefore, a concentration of the target protein to be measured can be calculated from a color value obtained by measurement, by using a plurality of reference samples in which a concentration of a target protein to be measured and a color value thereof are known and creating in advance a calibration curve indicating a correspondence between the concentration of the target protein to be measured and the color value in each reference sample.

The measurement of the color value depends on the method of coloring the target protein to be measured, but can be appropriately performed by a known method, and is not limited. For example, the measurement is performed by a L*a*b* color system, a L*c*h* color system, a L*u*v* color system, a Hunter Lab color system, an XYZ (Yxy) color system, a Munsell color system, or the like.

These color values can be measured by a color difference meter. Moreover, for example, a color value of the target protein to be measured may be also obtained by comparing a coloration determination sheet created for each of various color values with an actual coloration state of the protein.

In the method for calculating a protein concentration of the present invention, it is particularly preferable to adopt the Bradford method as a color reaction and to set the color value to be a b value defined in a L*a*b* color system based on a CIE standard. The L*a*b* color system is also adopted in JIS Z8729.

Figure 12:
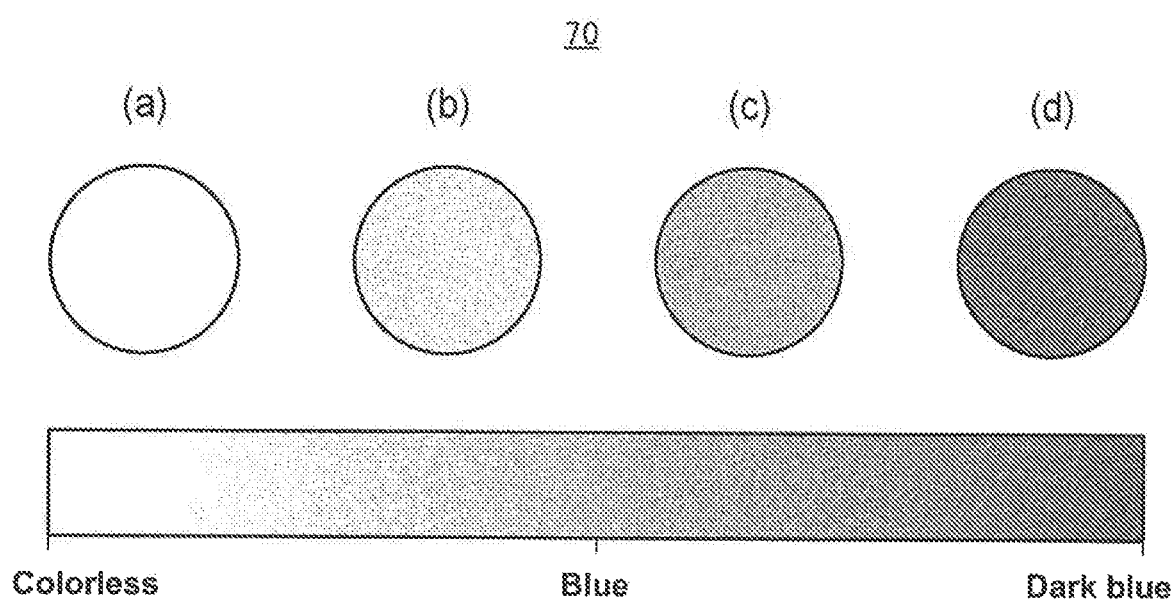
FIG. 12 is a diagram illustrating a coloration determination sheet which enables detection of a protein in the detection kit of the present invention.

The b value can be measured by the color difference meter. Moreover, for example, a b value of the target protein to be measured may be also obtained by comparing a coloration determination sheet created for each of various b values with an actual coloration state of the protein. FIG. 12 is a diagram illustrating an example of the coloration determination sheet. A coloration determination sheet 70 shows filter paper colored from colorless to dark blue as shown in (a) to (d) in a simulated manner, for example, and a b value is assigned to each color (not shown). The number of coloration determination sheets is not limited, and it is preferable that a b value can be more accurately obtained because the increase of the number of sheets causes that a large number of b values are assigned. The concentration of the target protein to be measured can be calculated by applying the b value obtained in this manner to the calibration curve created in advance.

In the concentration calculation method of the present invention, the concentration of the target protein to be measured in the sample can be calculated by applying the measured color value to the calibration curve, even when the concentration is about 0.25 ppb, depending on the kind of the target protein to be measured. Preferred examples of the concentration include 0.25 ppb or more, 0.5 ppb or more, 1 ppb or more, 2 ppb or more, 5 ppb or more, and 10 ppb or more. Moreover, the upper limit is not limited, but is 2,000 ppm or less, for example.

In addition, the detection method of the present invention can be commercialized for a kit for detecting a protein, for example, by combining a coloring agent or the like used in the coloration step, a filter used in the filtration step, and as necessary, a detecting agent used in the detection step or a gauge used to determine detection. In this case, even in a situation where a laboratory instrument, a material, or the like is not available, the detection method of the present invention can be simply and rapidly used, and is very suitable, in particular, for use in a factory.

Figure 10:
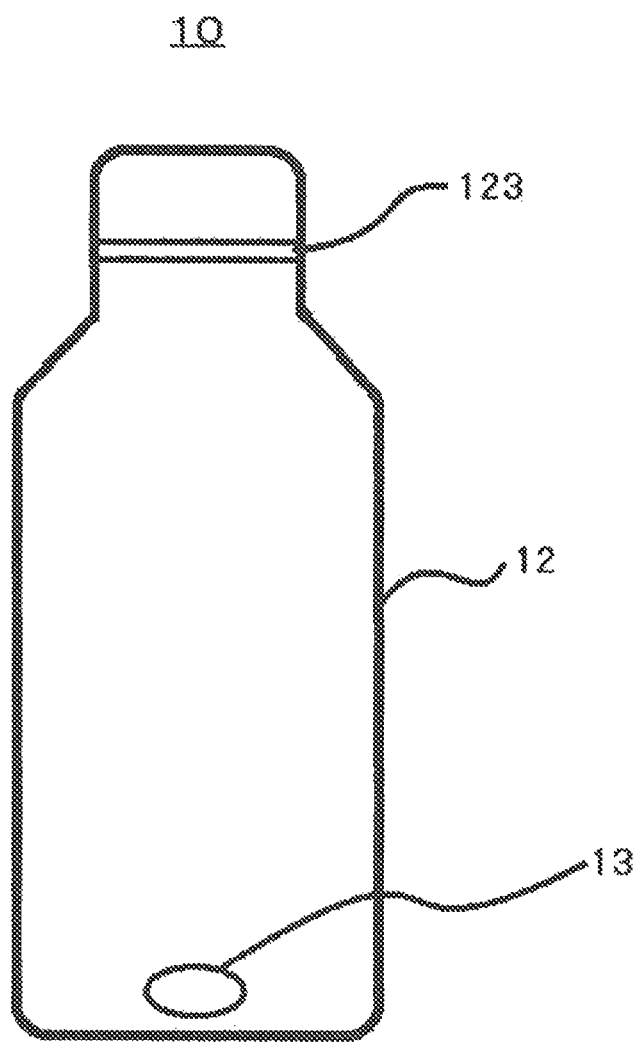
FIG. 10 is a diagram illustrating one embodiment of a detection kit of the present invention.

Specifically, one embodiment of the detection kit of the present invention includes, as shown in FIG. 10, a filter 123 for filtering, retaining, and concentrating a target protein to be measured, a sample introduction container 12, and a coloring agent 13 used in the coloration step. Moreover, a coloration determination sheet for measuring the concentration of the target protein to be measured may be included. As described above, the concentration of the target protein to be measured can be measured by comparing the coloration determination sheet with a coloration state of the protein detected on the filter.

Hereinafter, a method of using the detection kit 10, for a rinse liquid as a sample, will be described.

First, a rinse liquid, which is a sample, is introduced into the sample introduction container 12. The rinse liquid may be mixed with the coloring agent at the same time as the rinse liquid is introduced into the sample introduction container 12 (FIG. 10) by storing the coloring agent 13 in the sample introduction container 12 in advance. Or the coloring agent 13 may be added to the rinse liquid in the sample introduction container 12 after the sample introduction container 12 is filled with the rinse liquid. Alternatively, without using the coloring agent at this time, the coloring agent may be used in a coloration step after filtration described later.

Subsequently, the filter 123 is fixed near an upper portion of the sample introduction container 12. Thereafter, filtration is performed by passing the rinse liquid, which is the sample, through the filter by any method, and thus a target protein to be measured is retained and concentrated on the filter. At this time, if the coloring agent 13 is not used yet, the coloring agent 13 may be applied to the target protein to be measured which has been retained and concentrated on the filter. The application method can be appropriately selected according to the kind of the coloring agent 13. By doing so, the target protein to be measured retained and concentrated on the filter can be detected.

In addition, the detection kit of the present invention includes a coloring unit which colors a target protein to be measured, a filtering unit which filters the target protein to be measured with a filter, and a detecting unit which detects coloration of the target protein to be measured on the filter, and can be considered to be configured to enable detection of the protein from a coloration state of the filter. Furthermore, the above-described coloration determination sheet may be included therein.

Figure 11:
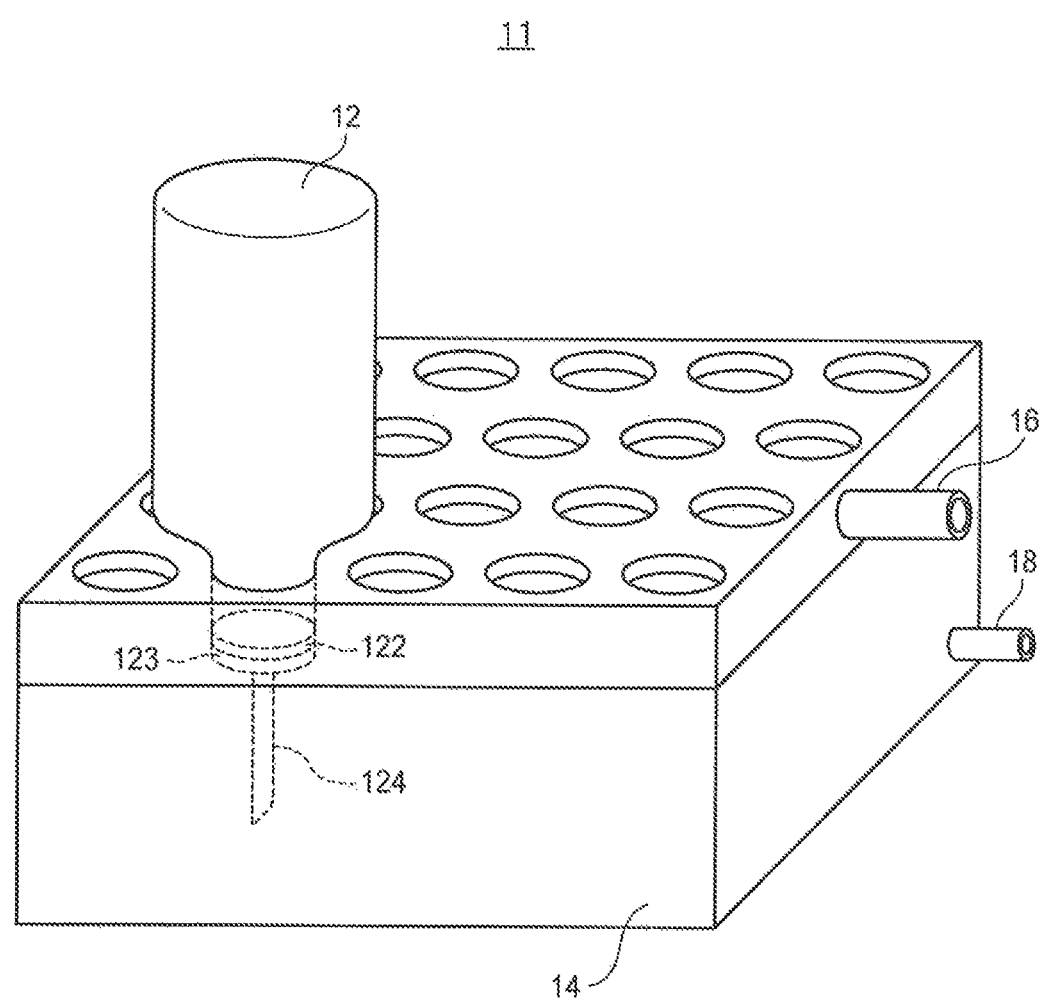
FIG. 11 is a diagram illustrating another embodiment of the detection kit of the present invention.

Examples of another embodiment of the detection kit of the present invention include an embodiment in which a plurality of sample introduction containers 12 are provided to simultaneously detect proteins in a plurality of samples. Specifically, for example, as shown in FIG. 11, a detection kit 11 includes a sample introduction container 12, a filter 123, a filtrate housing container 14, a pressure-reducing port 16, and a filtrate discharge port 18. Moreover, only one sample introduction container 12 is shown in FIG. 11, but a plurality of sample introduction containers 12 may be included as necessary.

First, for example, a plurality of rinse liquids sampled from a factory are respectively introduced into the sample introduction containers 12. For example, a filter fixing tool 122 is provided below the sample introduction container, and a filter such as a glass filter is installed therein. By connecting the pressure-reducing port 16 to an aspirator (not shown) and reducing pressure inside of the filtrate housing container 14, a target protein to be measured contained in the rinse liquid is concentrated on the glass filter and filtrate is discharged from a filtrate outlet 124 into the filtrate housing container 14. The filtrate discharge port 18 is usually closed, and when a storage amount of the filtrate in the filtrate housing container 14 increases, the filtrate discharge port 18 is appropriately opened to discharge the filtrate to the outside of the filtrate housing container 14.

When the coloring agent is a Bradford reagent, examples of an addition procedure thereof include adding a predetermined amount of the Bradford reagent in advance to the rinse liquid and then introducing the resultant into the sample introduction container 12; introducing the rinse liquid into the sample introduction container 12 and adding the Bradford reagent thereto; and adding the Bradford reagent to the glass filter after filtration of the rinse liquid is completed.

After the steps are completed, for example, by taking out the glass filter and comparing the glass filter with the coloration determination sheet, shown in FIG. 12, prepared in advance, a concentration of the target protein to be measured can be measured. Besides this method, a b value of the taken-out glass filter may be directly measured with a differential colorimeter, and a concentration of the target protein to be measured may be calculated from the calibration curve.

EXAMPLES

Hereinafter, the present invention will be more specifically described based on examples. These examples do not limit the present invention.

Example 1

2 mg/mL of a bovine serum albumin (BSA) standard reagent (produced by TAKARA) was diluted to prepare BSA solutions of 0.05 ppm, 0.1 ppm, and 0.15 ppm. 100 μL of a Bradford reagent (produced by TAKARA) was added to 10 mL of each solution, and the mixture was allowed to stand still at room temperature (25° C.) for 5 minutes and then was passed through a glass filter for 5 seconds. Three types of the glass filters, which are "GF-75" (manufactured by ADVANTEC MFS, INC., retained particle diameter: 0.3 μm), "GF/F" (manufactured by Whatman, retained particle diameter: 0.7 μm), and "GF/B" (manufactured by Whatman, retained particle diameter: 1.0 μm), were prepared and were used in the examination. Blue coloration on each filter was measured with a differential colorimeter (CR-5, manufactured by Konica Minolta, Inc.), and was evaluated with the obtained b values.

The results are shown in FIG. 1. In all the glass filters used in the examination, the blue coloration was observed, and the coloration showed BSA concentration dependence (that is, the coloration proceeded depending on a concentration of BSA). Therefore, it was revealed that a protein in a liquid can be simply detected by the detection method of the present invention.

Example 2

In the same manner as in Example 1, a BSA solution of 0.1 ppm was prepared, 100 μL of the Bradford reagent (produced by TAKARA) was added to 10 mL of the solution, and the mixture was allowed to stand still at room temperature (25° C.) for 5 minutes and then was passed through a glass filter "GF/B" (manufactured by Whatman) for 5 seconds. Blue coloration on the filter was measured with the differential colorimeter (CR-5, manufactured by Konica Minolta, Inc.) 0, 10, 20, 30, 40, 50, 60, 75, 90, and 105 minutes after the solution was passed, and was evaluated with the obtained b values.

Figure 2:
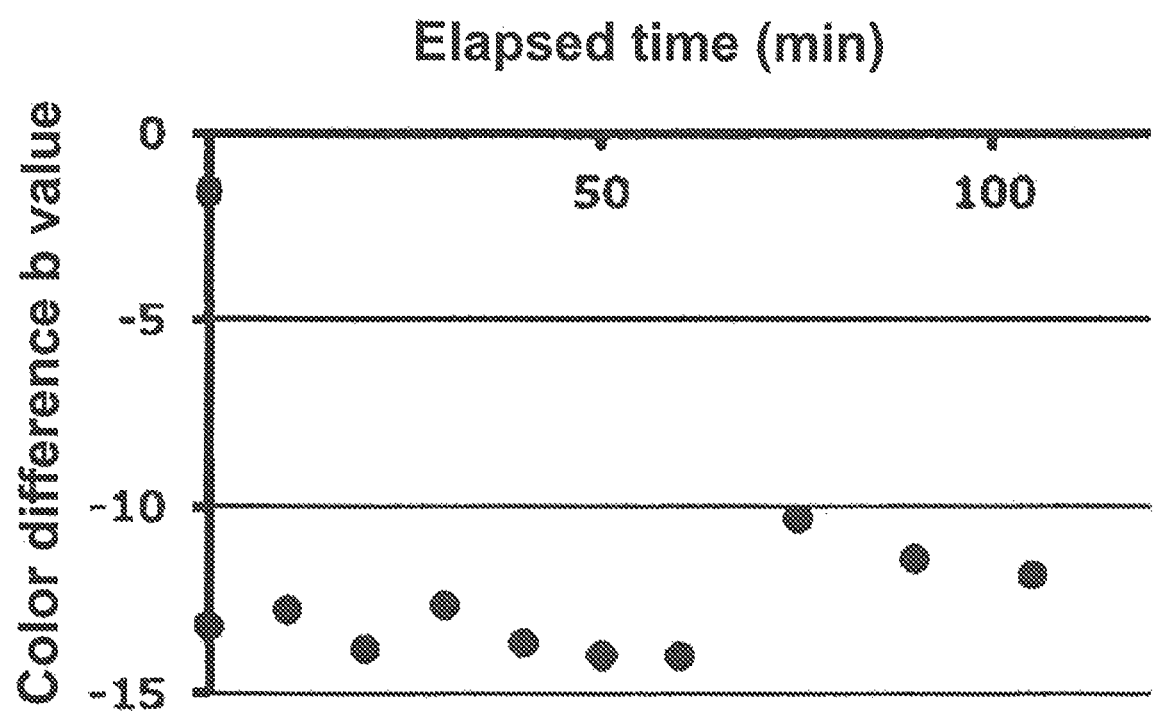
FIG. 2 is a graph showing results obtained by measuring a bovine serum albumin solution by the detection method of the present invention while changing a time after coloration and measuring blue coloration as a b value with the differential colorimeter in Example 2.

The results are shown in FIG. 2. According to the results, blue coloration stably occurred immediately after the liquid was passed and stable blue coloration was observed up to 60 minutes. Therefore, it was revealed that a protein in a liquid can be rapidly detected by the detection method of the present invention. In addition, it was revealed that color fading does not occur if measurement is performed within 60 minutes.

Example 3

Respective solutions containing 1 ppm protein of one of 6 items of allergen-specific raw materials (egg: ovalbumin, milk: casein, wheat: gliadin, buckwheat: partially purified buckwheat protein, peanut: partially purified peanut protein, and crustacean: crustacean tropomyosin), 1 ppm gelatin, and 1 ppm BSA were prepared, 100 μL of the Bradford reagent (produced by TAKARA) was added to 10 mL of each solution, and the mixture was allowed to stand still at room temperature (25° C.) for 5 minutes and then was passed through the glass filter "GF/B" (manufactured by Whatman) for 5 seconds. Blue coloration on each filter was measured with the differential colorimeter (CR-5, manufactured by Konica Minolta, Inc.), and was evaluated with the obtained b values.

Figure 3:
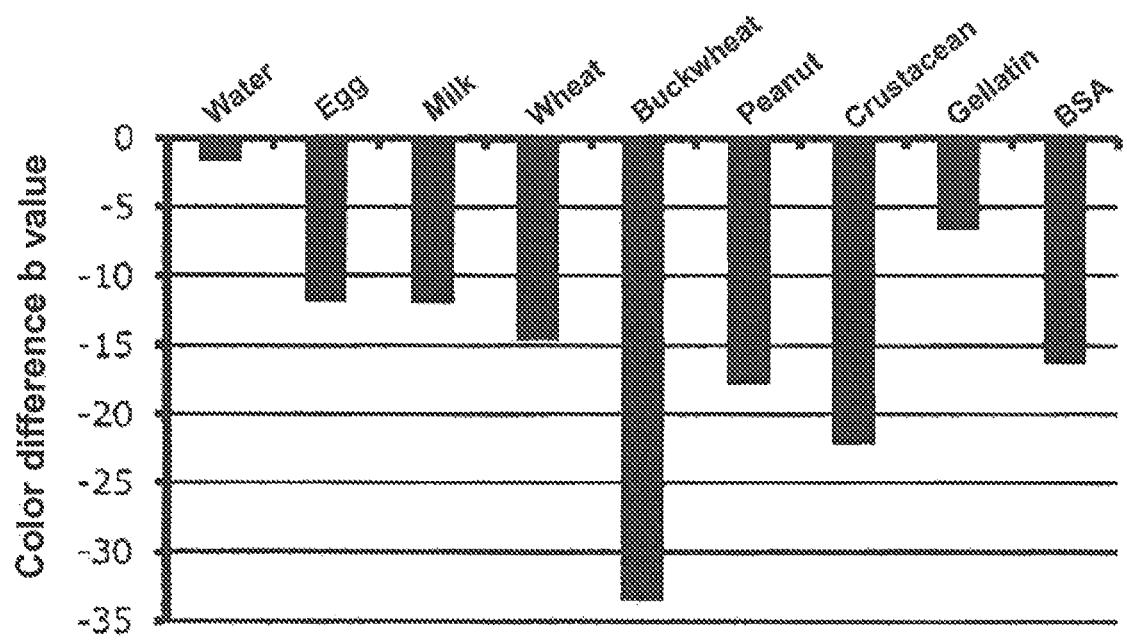
FIG. 3 is a graph showing results obtained by measuring proteins (egg, milk, wheat, buckwheat, peanut, crustacean, gelatin, and bovine serum albumin) of various allergens by the detection method of the present invention and measuring blue coloration as a b value with the differential colorimeter in Example 3.

The results are shown in FIG. 3. According to the results, the proteins of all the allergens could also be detected by the detection method of the present invention. Therefore, it was revealed that proteins in various kinds of liquids can be detected by the detection method of the present invention.

Example 4

10 ppb and 100 ppb of gelatin solutions were prepared, 1 mL of the Bradford reagent (produced by TAKARA) was added to 100 mL of each solution, and the mixture was allowed to stand still at room temperature (25° C.) for 5 minutes and then was passed through the glass filter "GF/B" (manufactured by Whatman) for 40 minutes. A filtration diameter of the glass filter "GF/B" when the solution was passed was 8 mm in measurement of the solution of 10 ppb and was 33 mm in measurement of the solution of 100 ppb. Blue coloration on each filter was measured with the differential colorimeter (CR-5, manufactured by Konica Minolta, Inc.), and was evaluated with the obtained b values. A diameter of a measurement port of the differential colorimeter for color difference measurement was 3 mm in measurement of the solution of 10 ppb and was 30 mm in measurement of the solution of 100 ppb.

The results are shown in Table 1. According to the results, even gelatin, which is known to be difficult to detect, could be detected by the detection method of the present invention without any problem. Therefore, it was revealed that a protein in a liquid which is difficult to detect by the method in the related art can be detected by the detection method of the present invention.

TABLE 1

| Concentration of gelatin | 100 ppb | 10 ppb |
|---|---|---|
| Filtration diameter | 33 mm | 8 mm |
| Diameter of measurement port | 30 mm | 3 mm |
| Sample volume | 100 mL | |
| b value | −3.96 ± 0.27 | −9.17 ± 0.81 |
| Visual evaluation | Blue can be observed | Blue can be observed |

Example 5

Example 5-1

A milk allergen (Sodium Caseinate) was diluted to prepare 10 ppb, 20 ppb, 30 ppb, 40 ppb, 50 ppb, and 100 ppb of solutions. 100 µL of a Bradford reagent (produced by TAKARA) was added to 100 mL of each solution, and the mixture was allowed to stand still at room temperature (25° C.) for 5 minutes and then was passed through a glass filter for 40 minutes. As the glass filter, "GF/F" (manufactured by Whatman, retained particle diameter: 0.7 µm, filtration diameter: 8 mm) was used. Blue coloration on each filter was measured with the differential colorimeter (CR-5, manufactured by Konica Minolta, Inc.), and was evaluated with the obtained b values.

Example 5-2

A milk allergen (Sodium Caseinate) was diluted to prepare solutions of 0.1 ppm, 0.5 ppm, 1 ppm, and 2 ppm. 100 µL of the Bradford reagent (produced by TAKARA) was added to 10 mL of each solution, and the mixture was allowed to stand still at room temperature (25° C.) for 5 minutes and then was passed through a glass filter for 5 seconds. As the glass filter, "GF/F" (manufactured by Whatman, retained particle diameter: 0.7 µm, filtration diameter: 15 mm) was used. Blue coloration on each filter was measured with the differential colorimeter (CR-5, manufactured by Konica Minolta, Inc.), and was evaluated with the obtained b values.

Figure 4:
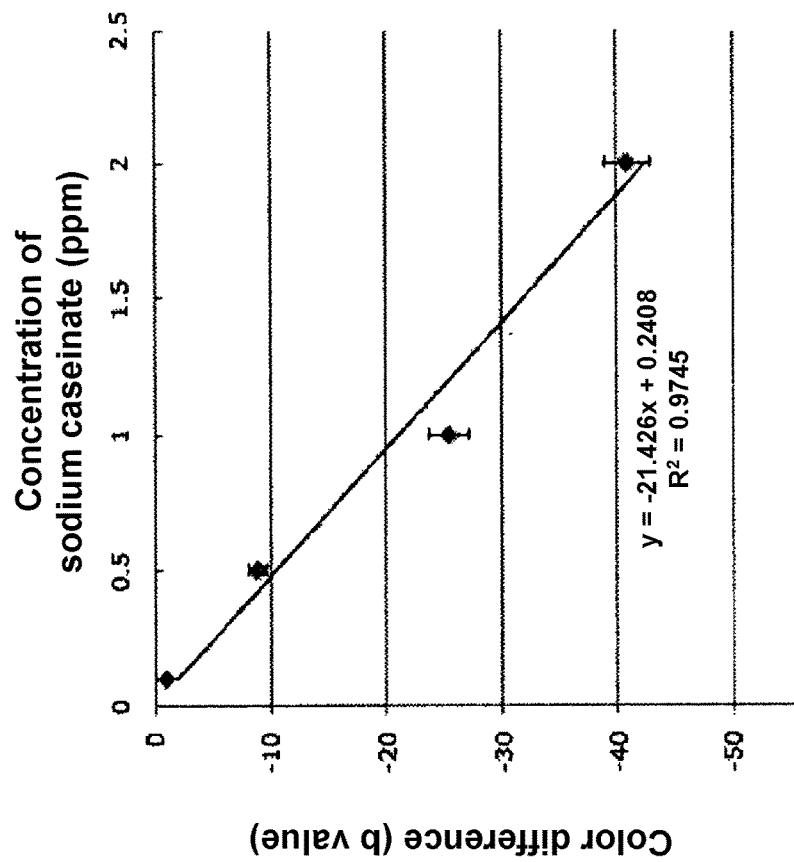
FIG. 4 provides graphs (A) and (B) showing results obtained by measuring a milk allergen (casein) and measuring blue coloration as a b value with the differential colorimeter in Example 5.
Figure 4:
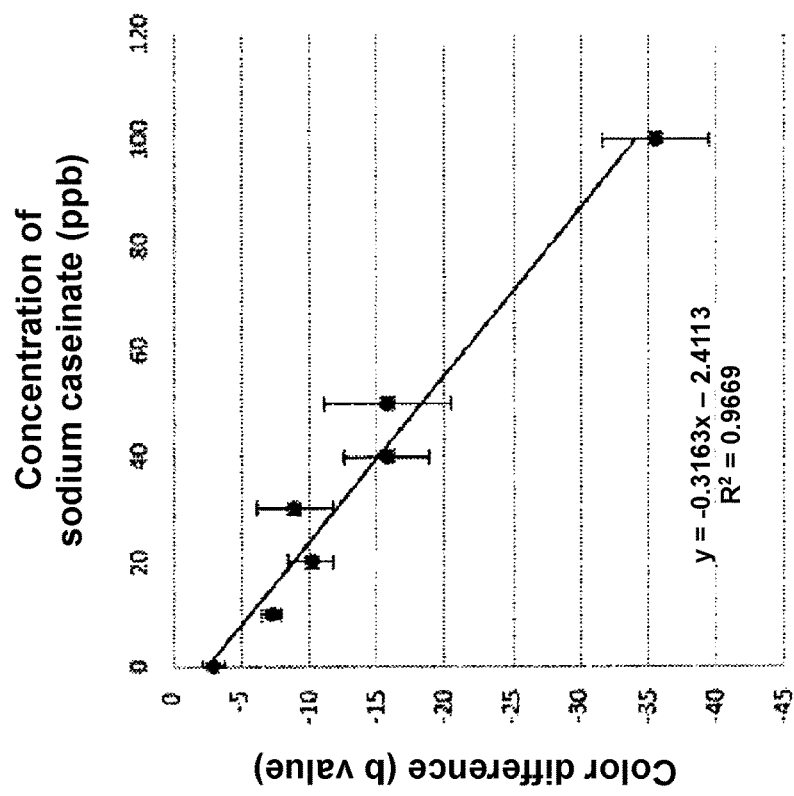

The results of Example 5-1 are shown in (A) of FIG. 4 and the results of Example 5-2 are shown in (B) of FIG. 4. According to the results, milk allergens with a wide range of concentrations, including a milk allergen in low concentration, could be detected by using the detection method of the present invention. Moreover, a correlation ship between the concentration of the milk allergen and the b value could be confirmed.

Example 6

Example 6-1

An egg allergen (ovalbumin) was diluted to prepare 10 ppb, 20 ppb, 50 ppb, and 100 ppb of solutions. Thereafter, an experiment was performed in the same manner as in Example 5-1. Blue coloration on each filter was measured with the differential colorimeter (CR-5, manufactured by Konica Minolta, Inc.), and was evaluated with the obtained b values.

Example 6-2

In addition, an egg allergen (ovalbumin) was diluted to prepare solutions of 0.25 ppm, 0.5 ppm, 1 ppm, and 1.5 ppm. Thereafter, an experiment was performed in the same manner as in Example 5-2. Blue coloration on each filter was measured with the differential colorimeter (CR-5, manufactured by Konica Minolta, Inc.), and was evaluated with the obtained b values.

Figure 5:
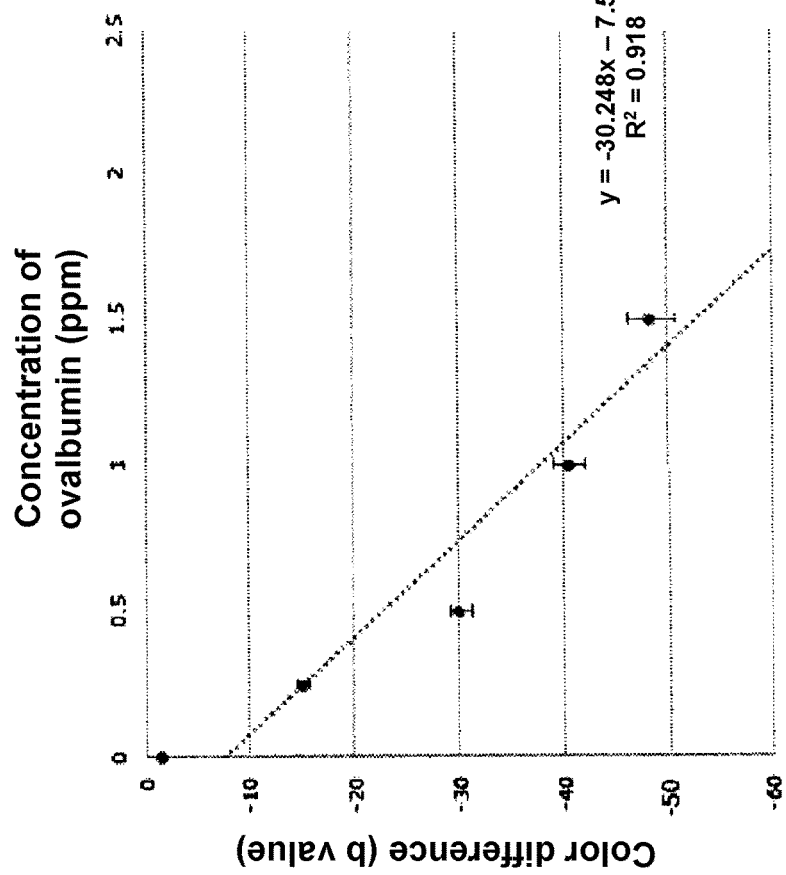
FIG. 5 provides graphs (A) and (B) showing results obtained by measuring an egg allergen (ovalbumin) and measuring blue coloration as a b value with the differential colorimeter in Example 6.
Figure 5:
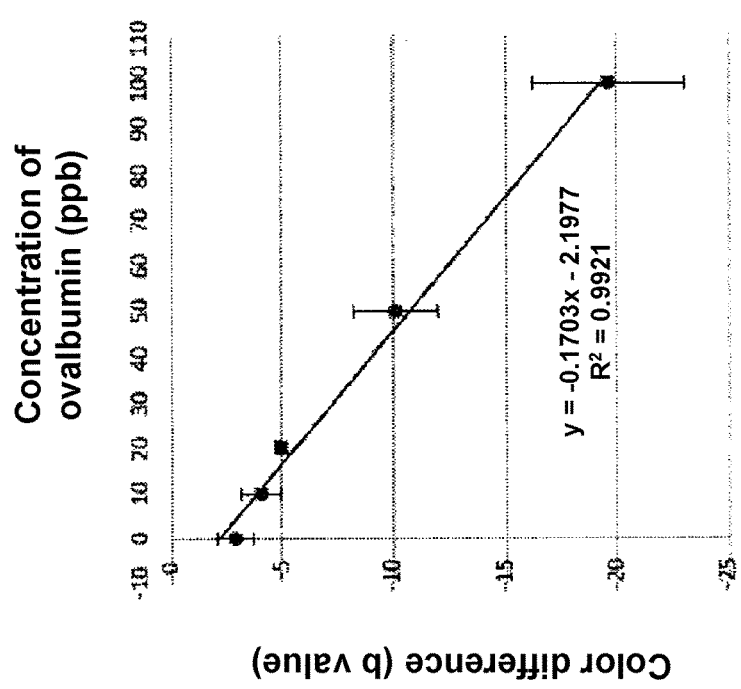

The results of Example 6-1 are shown in (A) of FIG. 5 and the results of Example 6-2 are shown in (B) of FIG. 5. According to the results, egg allergens with a wide range of concentrations, including an egg allergen in low concentration, could be detected by using the detection method of the present invention. Moreover, a correlation between the concentration of the egg allergen and the b value could be confirmed.

Example 7

A wheat allergen (gliadin) was diluted to prepare solutions of 0.25 ppb, 0.5 ppb, and 1 ppb. Thereafter, an experiment was performed in the same manner as in Example 5-1. Blue coloration on each filter was measured with the differential colorimeter (CR-5, manufactured by Konica Minolta, Inc.), and was performed with the obtained b values.

Figure 6:
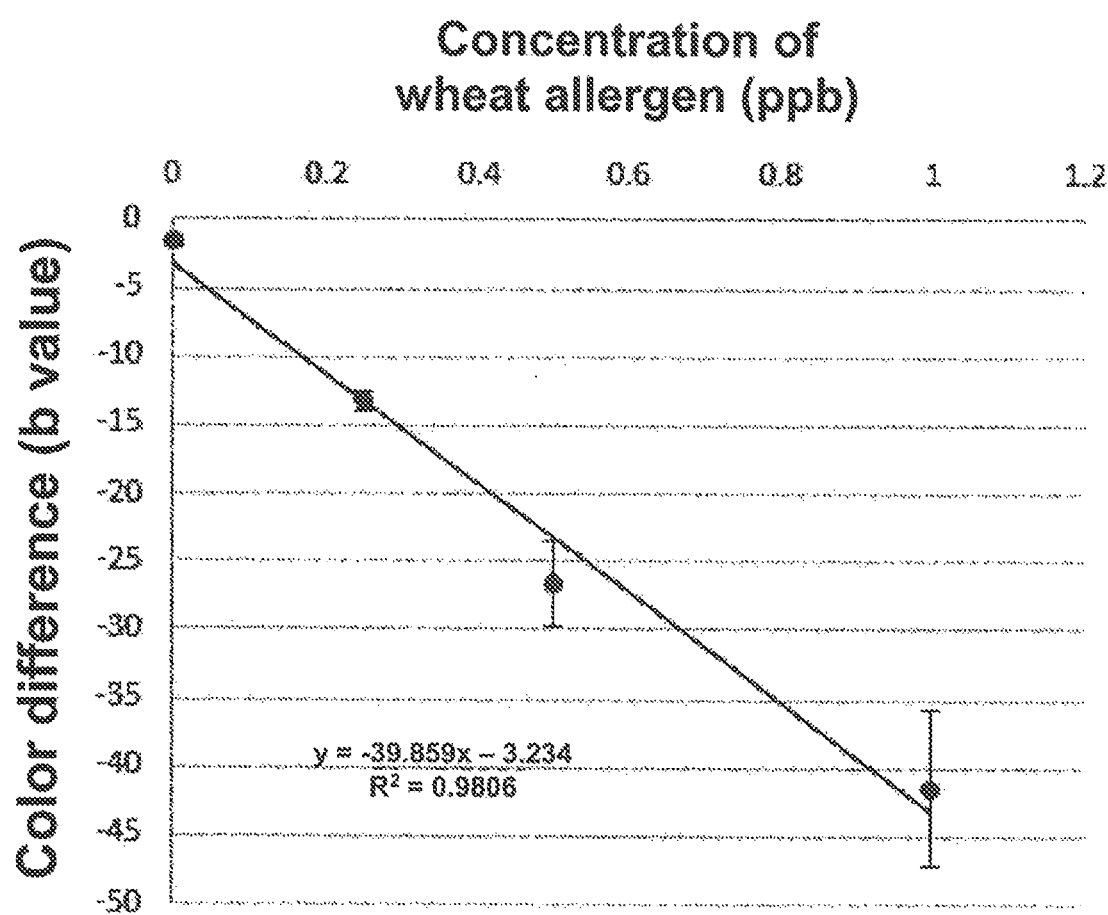
FIG. 6 is a graph showing results obtained by measuring a wheat allergen (gliadin) and measuring blue coloration as a b value with the differential colorimeter in Example 7.

The results are shown in FIG. 6. According to the results, a wheat allergen in low concentration could be detected by using the detection method of the present invention. Moreover, a correlationship between the concentration of the wheat allergen and the b value could be confirmed.

Example 8

A buckwheat allergen (partially purified buckwheat protein) was diluted to prepare solutions of 10 ppb, 20 ppb, and 30 ppb. Thereafter, an experiment was performed in the same manner as in Example 5-1. Blue coloration on each filter was measured with the differential colorimeter (CR-5, manufactured by Konica Minolta, Inc.), and was evaluated with the obtained b values.

Figure 7:
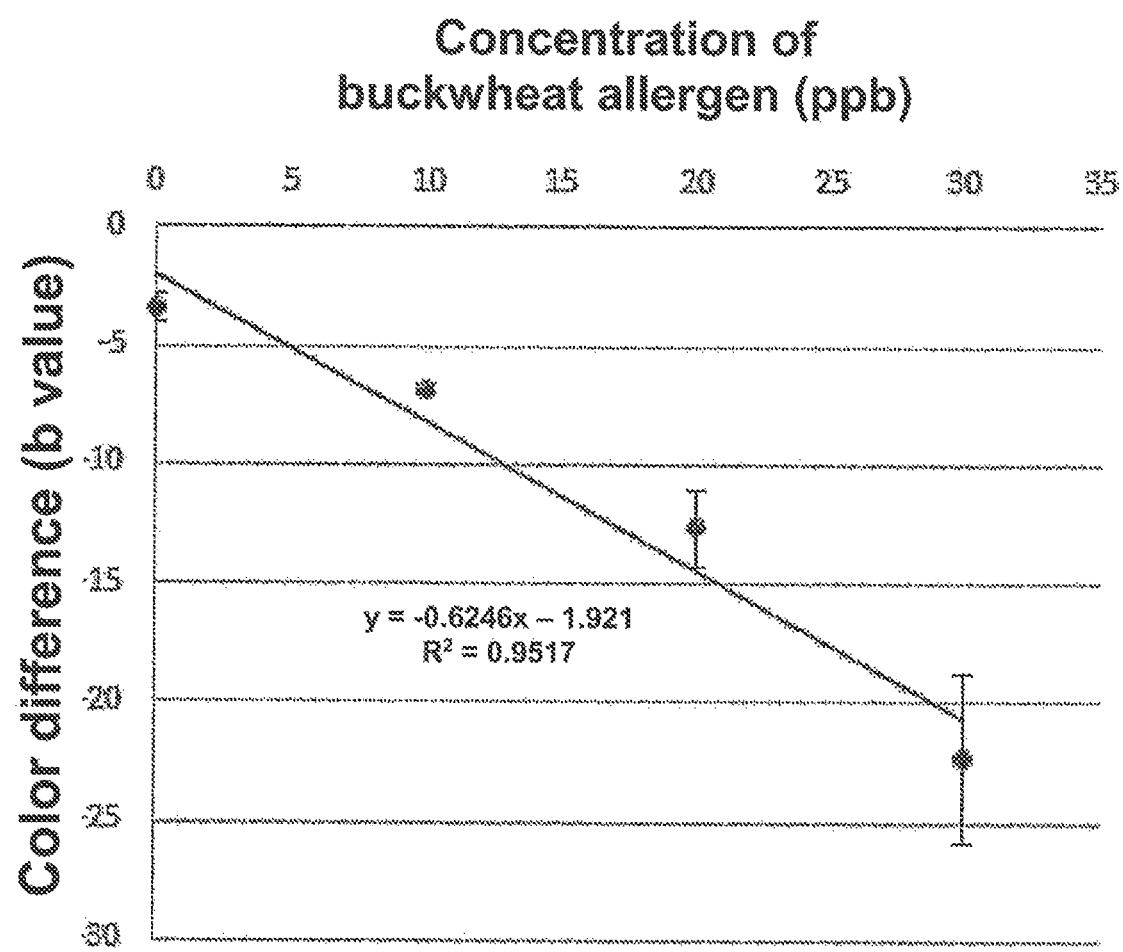
FIG. 7 is a graph showing results obtained by measuring a buckwheat allergen (partially purified buckwheat protein) and measuring blue coloration as a b value with the differential colorimeter in Example 8.

The results are shown in FIG. 7. According to the results, a buckwheat allergen in low concentration could be detected by using the detection method of the present invention. Moreover, a correlationship between the concentration of the buckwheat allergen and the b value could be confirmed.

Example 9

A peanut allergen (partially purified peanut protein) was diluted to prepare solutions of 5 ppb, 10 ppb, and 20 ppb. Thereafter, an experiment was performed in the same manner as in Example 5-1. Blue coloration on each filter was measured with the differential colorimeter (CR-5, manufactured by Konica Minolta, Inc.), and was evaluated with the obtained b values.

Figure 8:
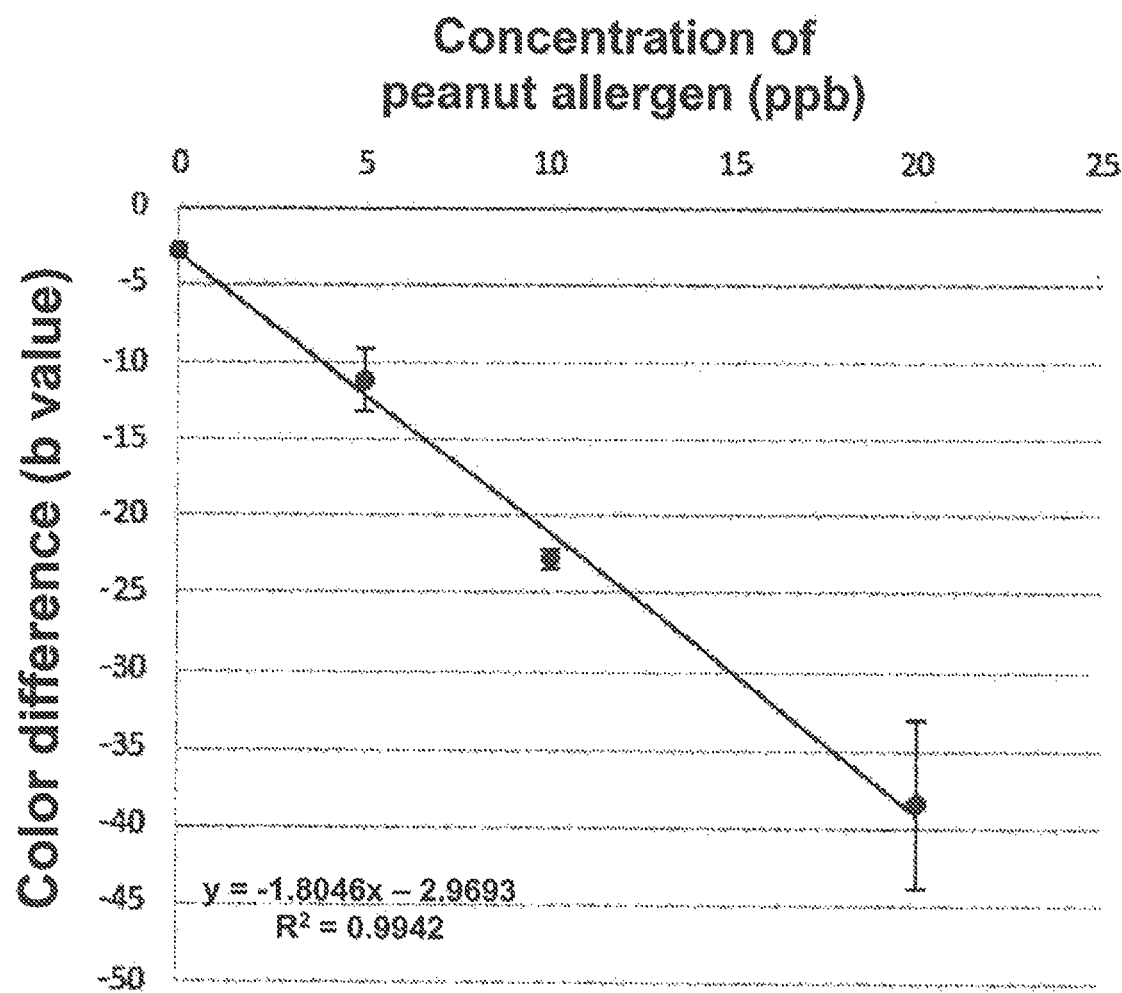
FIG. 8 is a graph showing results obtained by measuring a peanut allergen (partially purified peanut protein) and measuring blue coloration as a b value with the differential colorimeter in Example 9.

The results are shown in FIG. 8. According to the results, a peanut allergen with a low concentration could be detected by using the detection method of the present invention.

Moreover, a correlationship between the concentration of the peanut allergen and the b value could be confirmed.

Example 10

A crustacean allergen (crustacean tropomyosin) was diluted to prepare 0.25 ppb, 0.5 ppb, 1 ppb, and 2 ppb of solutions. Thereafter, an experiment was performed in the same manner as in Example 5-1. Blue coloration on each filter was measured with the differential colorimeter (CR-5, manufactured by Konica Minolta, Inc.), and evaluations were performed with the obtained b values.

Figure 9:
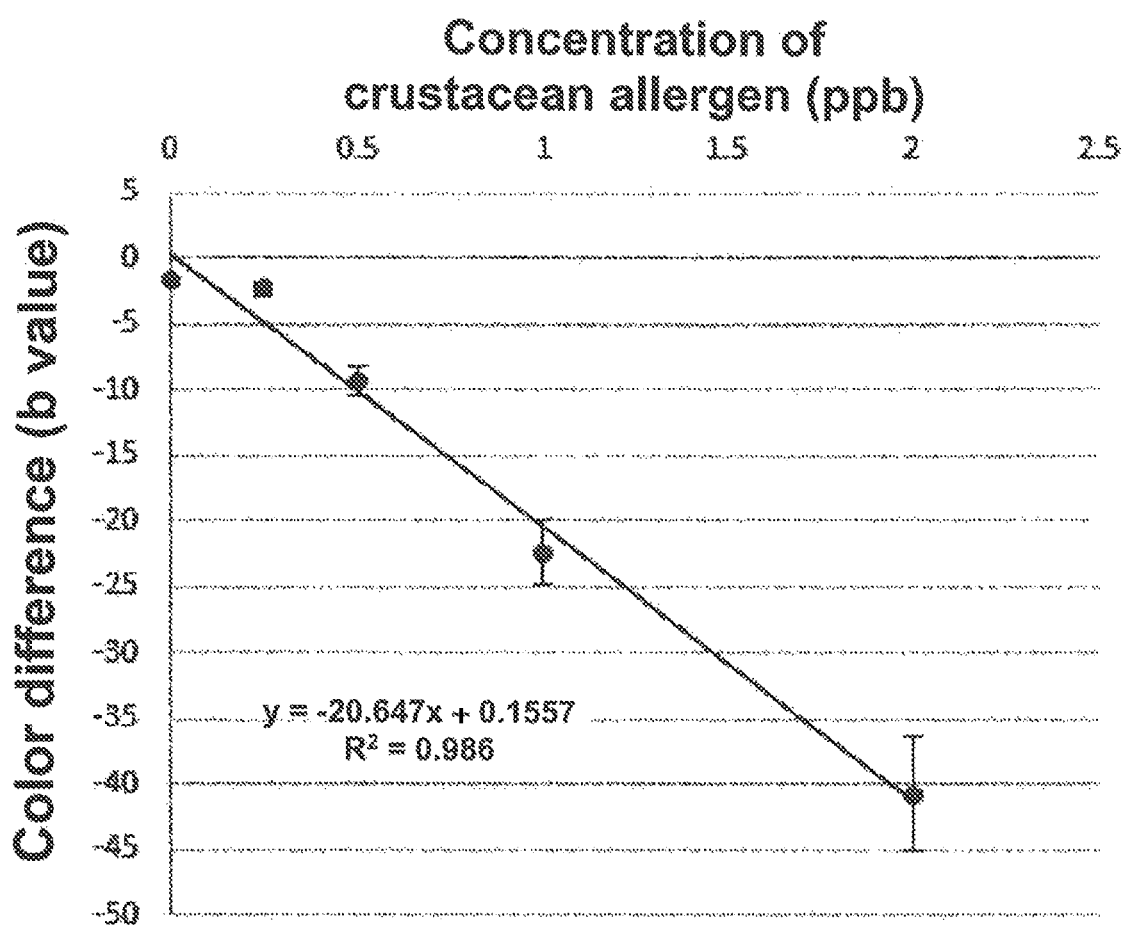
FIG. 9 is a graph showing results obtained by measuring a crustacean allergen (crustacean tropomyosin) and measuring blue coloration as a b value with the differential colorimeter in Example 10.

The results are shown in FIG. 9. According to the results, a crustacean allergen in low concentration could be detected by using the detection method of the present invention. Moreover, a correlationship between the concentration of the crustacean allergen and the b value could be confirmed.

Example 11

Rinse water after cleaning an ice cream production facility was collected, and a protein was detected using the detection kit and the coloration determination sheet which are shown in FIGS. 11 and 12.

100 μL of the Bradford reagent (produced by TAKARA) was added to 10 mL of the rinse water, the mixture was allowed to stand still at room temperature (25° C.) for 5 minutes and then was introduced into the sample introduction container 12. Air in the filtrate housing container 14 was sucked from the pressure-reducing port 16 to be in a reduced-pressure state, by operating an aspirator (not shown). By doing so, a target protein to be measured contained in the rinse liquid was concentrated on the glass filter, and filtrate was discharged from the filtrate outlet 124 into the filtrate housing container 14. Moreover, as the glass filter, "GF/F" (manufactured by Whatman, retained particle diameter: 0.7 μm, filtration diameter: 15 mm) was used. After the above steps are completed, the glass filter was taken out, and the blue coloration on the glass filter was compared with (a) to (d) of the coloration determination sheet 70. As a result, the blue coloration of the glass filter was almost the same as (c) of the coloration determination sheet 70, and from the protein concentration of (c) which was examined in advance by performing the steps under the same conditions as above, the concentration of the protein in the rinse water was found to be about 1.4 ppm.

The results are shown in Table 2. Table 2 also shows the b value of the glass filter after coloration, which is measured with the differential colorimeter (CR-5, manufactured by Konica Minolta, Inc.). Furthermore, the time required for detection (time from the installation of the test instrument to the detection) was 10 minutes.

TABLE 2

| Water sampling place | Ice cream production facility |
| --- | --- |
| Kind of residual allergen | Egg protein |
| Sample | Rinse water |
| Color difference b value | −42.56 |
| ELISA (egg protein) | 1.4 ppm |
| ELISA (milk casein) | Detection limit or less |
| LC-MS/MS | 1.9 ppm |

In Table 2, the results measured by the ELISA method are also showed. From Table 2, the protein was turned out to be an egg protein. Furthermore, as a result of analyzing the rinse water by LC-MS/MS (liquid chromatography-mass spectrometry), the concentration of the egg protein in the rinse water was 1.9 ppm.

The present invention has been described in detail with the specific embodiments, but it is apparent to those skilled in the art that various modifications and variations can be made without departing from the spirit and the scope of the present invention. Moreover, the present application is based on a Japanese patent application (Japanese Patent Application No. 2017-216909) filed on Nov. 10, 2017, which is incorporated by reference in its entirety.

INDUSTRIAL APPLICABILITY

According to the present invention, a protein in a liquid can be simply detected and measured. In particular, allergens, such as gelatin and collagen, for which a simple measurement method is not known can also be simply detected and measured with reduced labor or cost. Particularly in the food industry, the detection method of the present invention is very useful for grasping an amount of an allergen in rinse water after cleaning of a production facility in a factory, and has extremely high industrial applicability.

REFERENCE SIGNS LIST 10, 11: Detection kit
12: Sample introduction container
122: Filter fixing tool
123: Filter
124: Filtrate outlet
13: Coloring agent
14: Filtrate housing container
16: Pressure-reducing port
18: Filtrate discharge port
70: Coloration determination sheet

The invention claimed is:

1. A method for detecting a protein comprising:
obtaining rinse water at the time of cleaning in a food production factory;
coloring a target protein to be measured in the rinse water, wherein the target protein is gelatin or collagen;
filtering the target protein to be measured by passing the rinse water through a filter and producing a filtrate; and
detecting coloration of the target protein to be measured on the filter.

2. The method according to claim 1, wherein the coloring, the filtering and the detecting are performed in this order.

3. The method according to claim 1, wherein the filtering, the coloring and the detecting are performed in this order.

4. The method according to claim 1, wherein in the coloring, coloration of the target protein to be measured is performed by using a reagent for measurement causing a shift of an absorbance wavelength by binding to the target protein to be measured.

5. The method according to claim 4, wherein the coloring is coloring the target protein to be measured by a Bradford method.

6. The method according to claim 1, wherein the filtering is filtering the target protein to be measured with a glass filter.

7. The method according to claim 1, wherein a time required for detection is 1 hour or shorter.

8. A method for calculating a protein concentration comprising:
obtaining rinse water at the time of cleaning in a food production factory;

coloring a target protein to be measured in the rinse water, wherein the target protein is gelatin or collagen;

filtering the target protein to be measured by passing the rinse water through a filter and producing a filtrate;

detecting coloration of the target protein to be measured on the filter; and measuring a color value of the coloration of the target protein to be measured which is detected in the detecting, wherein a concentration of the target protein to be measured is calculated from the color value measured in the measuring by using a plurality of reference samples in which a concentration of a target protein to be measured and a color value thereof are known and creating a calibration curve indicating a correspondence between the concentration of the target protein to be measured and the color value in each reference sample.

9. A method for calculating a protein concentration comprising:

obtaining rinse water at the time of cleaning in a food production factory;

coloring a target protein in the rinse water to be measured by a Bradford method, wherein the target protein is gelatin or collagen;

filtering the target protein to be measured by passing the rinse water through a filter and producing a filtrate;

detecting coloration of the target protein to be measured on the filter; and measuring a b value defined in a L*a*b* color system based on a CIE standard for the coloration of the target protein to be measured which is detected in the detecting, wherein a concentration of the target protein to be measured is calculated from the b value measured in the measuring by using a plurality of reference samples in which a concentration of a target protein to be measured and a b value defined in the L*a*b* color system based on the CIE standard are known and creating a calibration curve indicating a correspondence between the concentration of the target protein to be measured and the b value in each reference sample.

* * * * *